United States Patent
Okerlund et al.

(10) Patent No.: US 7,813,785 B2
(45) Date of Patent: *Oct. 12, 2010

(54) CARDIAC IMAGING SYSTEM AND METHOD FOR PLANNING MINIMALLY INVASIVE DIRECT CORONARY ARTERY BYPASS SURGERY

(75) Inventors: Darin R. Okerlund, Muskego, WI (US); Jasbir S. Sra, W305 N. 2963 Red Oak Ct., Pewaukee, WI (US) 53072; Laurent Launay, Saint Remy les chevreuse (FR); Melissa Vass, Milwaukee, WI (US)

(73) Assignees: General Electric Company, Schenectady, NY (US); Jasbir S. Sra, Pewaukee, WI (US)

( * ) Notice: Subject to any disclaimer, the term of this patent is extended or adjusted under 35 U.S.C. 154(b) by 953 days.

This patent is subject to a terminal disclaimer.

(21) Appl. No.: 10/708,564

(22) Filed: Mar. 11, 2004

(65) Prior Publication Data
US 2005/0004443 A1    Jan. 6, 2005

Related U.S. Application Data

(60) Provisional application No. 60/484,012, filed on Jul. 1, 2003.

(51) Int. Cl.
*A61B 5/05* (2006.01)
(52) U.S. Cl. ............... 600/425; 600/426; 600/429; 606/130
(58) Field of Classification Search ............... 600/417, 600/424, 425, 426, 427; 345/178, 634, 661; 606/130
See application file for complete search history.

(56) References Cited

U.S. PATENT DOCUMENTS 3,954,098 A    5/1976    Dick et al. ............... 128/2.05

(Continued)

FOREIGN PATENT DOCUMENTS

EP    0182619 A2    5/1986

(Continued)

OTHER PUBLICATIONS

Sra et al., "Registration of Three-Dimensional Left Atrial Computed Tomographic Images With Projection Images Obtained Using Fluoroscopy", Circulation 2005; 112: 3763-3768.

(Continued)

*Primary Examiner*—Long V Le
*Assistant Examiner*—Ellsworth Weatherby
(74) *Attorney, Agent, or Firm*—Cantor Colburn LLP (57) ABSTRACT

A method for planning minimally invasive direct coronary artery bypass (MIDCAB) for a patient includes obtaining acquisition data from a medical imaging system, and generating a 3D model of the coronary arteries and one or more cardiac chambers of interest. One or more anatomical landmarks are identified on the 3D model, and saved views of the 3D model are registered on an interventional system. One or more of the registered saved views are visualized with the interventional system.

24 Claims, 4 Drawing Sheets

U.S. PATENT DOCUMENTS

| | | | |
|---|---|---|---|
| 4,364,397 A | 12/1982 | Citron et al. | |
| 4,574,807 A | 3/1986 | Hewson et al. | 128/419 PG |
| 4,638,798 A * | 1/1987 | Shelden et al. | 606/130 |
| 5,245,287 A | 9/1993 | Nowak et al. | 324/322 |
| 5,274,551 A | 12/1993 | Corby, Jr. | 364/413.13 |
| 5,304,212 A | 4/1994 | Czeisler et al. | 607/88 |
| 5,348,020 A | 9/1994 | Hutson | 128/696 |
| 5,353,795 A | 10/1994 | Souza et al. | 128/653.2 |
| 5,391,199 A | 2/1995 | Ben-Haim | 607/122 |
| 5,431,688 A | 7/1995 | Freeman | 607/10 |
| 5,515,849 A | 5/1996 | Murashita et al. | |
| 5,568,384 A | 10/1996 | Robb et al. | 364/419.13 |
| 5,738,093 A | 4/1998 | Santi | 128/653.1 |
| 5,765,561 A | 6/1998 | Chen et al. | |
| 5,823,958 A | 10/1998 | Truppe | 600/426 |
| 5,839,440 A | 11/1998 | Liou et al. | 128/654 |
| 5,951,475 A | 9/1999 | Gueziec et al. | 600/425 |
| 6,058,218 A | 5/2000 | Cline | |
| 6,081,577 A | 6/2000 | Webber | 378/23 |
| 6,154,516 A | 11/2000 | Heuscher et al. | 378/15 |
| 6,208,347 B1 | 3/2001 | Migdal | 345/419 |
| 6,233,304 B1 | 5/2001 | Hu et al. | 378/8 |
| 6,235,038 B1 | 5/2001 | Hunter et al. | 606/130 |
| 6,246,898 B1 * | 6/2001 | Vesely et al. | 600/424 |
| 6,249,693 B1 | 6/2001 | Cline et al. | 600/410 |
| 6,252,924 B1 | 6/2001 | Davantes et al. | 378/8 |
| 6,256,368 B1 | 7/2001 | Hsieh et al. | 378/8 |
| 6,266,553 B1 | 7/2001 | Fluhrer et al. | 600/428 |
| 6,289,115 B1 | 9/2001 | Takeo | 382/130 |
| 6,289,239 B1 | 9/2001 | Panescu et al. | 600/523 |
| 6,314,310 B1 | 11/2001 | Ben-Haim et al. | 600/424 |
| 6,325,797 B1 | 12/2001 | Stewart et al. | 606/41 |
| 6,348,793 B1 | 2/2002 | Balloni et al. | 324/309 |
| 6,353,445 B1 | 3/2002 | Babula et al. | 345/733 |
| 6,381,485 B1 | 4/2002 | Hunter et al. | 600/407 |
| 6,389,104 B1 | 5/2002 | Bani-Hashemi et al. | 378/98.12 |
| 6,411,848 B2 | 6/2002 | Kramer et al. | 607/9 |
| 6,421,412 B1 | 7/2002 | Hsieh et al. | 378/9 |
| 6,456,867 B2 | 9/2002 | Reisfeld | 600/407 |
| 6,468,265 B1 | 10/2002 | Evans et al. | 606/1 |
| 6,490,475 B1 | 12/2002 | Seeley et al. | 600/426 |
| 6,490,479 B2 | 12/2002 | Bock | 600/518 |
| 6,493,575 B1 * | 12/2002 | Kesten et al. | 600/431 |
| 6,504,894 B2 | 1/2003 | Pan | 378/8 |
| 6,549,606 B1 | 4/2003 | Vaillant et al. | 378/4 |
| 6,556,695 B1 | 4/2003 | Packer et al. | 382/128 |
| 6,584,343 B1 | 6/2003 | Ransbury et al. | 600/509 |
| 6,650,927 B1 | 11/2003 | Keidar | 600/424 |
| 6,856,827 B2 * | 2/2005 | Seeley et al. | 600/426 |
| 6,950,689 B1 | 9/2005 | Willis et al. | |
| 7,047,060 B1 | 5/2006 | Wu | |
| 2002/0010392 A1 | 1/2002 | Desai | 600/374 |
| 2002/0042570 A1 | 4/2002 | Schaldach et al. | |
| 2002/0046756 A1 | 4/2002 | Laizzo et al. | 128/899 |
| 2002/0138105 A1 | 9/2002 | Kralik | 607/9 |
| 2003/0018251 A1 | 1/2003 | Solomon | 600/427 |
| 2003/0023266 A1 | 1/2003 | Borillo et al. | 606/200 |
| 2003/0028183 A1 | 2/2003 | Sanchez et al. | 606/34 |
| 2003/0097219 A1 | 5/2003 | O'Donnell et al. | 702/19 |
| 2003/0109780 A1 * | 6/2003 | Coste-Maniere et al. | 600/407 |
| 2003/0120264 A1 | 6/2003 | Lattouf | |
| 2003/0187358 A1 | 10/2003 | Okerlund et al. | 600/443 |
| 2003/0220557 A1 | 11/2003 | Cleary et al. | 600/409 |
| 2004/0027347 A1 | 2/2004 | Farsaie | 345/419 |
| 2004/0087850 A1 | 5/2004 | Okerlund et al. | 600/407 |
| 2004/0097806 A1 * | 5/2004 | Hunter et al. | 600/434 |
| 2004/0210125 A1 * | 10/2004 | Chen et al. | 600/407 |
| 2004/0225212 A1 | 11/2004 | Okerlund et al. | 600/407 |
| 2004/0225328 A1 | 11/2004 | Okerlund et al. | 607/9 |
| 2004/0225331 A1 | 11/2004 | Okerlund et al. | 607/14 |
| 2005/0059876 A1 * | 3/2005 | Krishnan et al. | 600/407 |

FOREIGN PATENT DOCUMENTS

| | | | |
|---|---|---|---|
| EP | 1182619 | * | 2/2002 |
| EP | 1182619 A2 | | 2/2002 |
| EP | 1321101 A2 | | 12/2002 |
| JP | 2002143179 A1 | | 5/2002 |
| WO | WO 91/07726 | | 5/1991 |
| WO | WO 96/10949 | | 4/1996 |

OTHER PUBLICATIONS

Toshiko Nakai, Michael D. Lesh, Edward P. Gerstenfeld, Renu Virmani, Russell Jones and Randall J. Lee; "Percutaneous Left Atrial Appendage Occlusion (PLAATO) for Preventing Cardioembolism: First Experience in Canine Model", Circulation 2002; 105;2217-2222; originally published online Apr. 15, 2002; American Heart Association; http://circ.ahajounals.org/cgi/content/full/105/18/2217.

PCT Search Report for PCT/US2004/020909.

F. H.M. Wittkampf et al.; "Loca Lisa—New Technique for Real-time 3-Dimensional Localization of Regular Intercardiac Electrodes;" *Circulationh*; 1999; 99: 1312-1317.

"Advanced Vessel Analysis" product descritpoin, [online] http://www.gehealthcare.com/usen/ct/clin_app/products/aswessel.html [retrieved Dec. 1, 2004].

"CardilQ" product description, [online], http://egems.gehealthcare.com/geCommunity/Europe/flex_trial/awFlexTrial/aw3_1/eflextrial [retrieved on Dec. 1, 2004].

Genevieve Derumeaux et al., Doppler Tissue Imaging Quantitates Regional Wall Motion During Myocardial Ischemia and Reperfusion, Circulation Journal of the American Heart Association, Circulation 1998; 97; 1970-1977.

Olivier Gerard et al., Efficient Model-Based Quantification of Left Ventricular Function in 3-D Echocardiography. IEEE Transactions on Medical Imaging, 21(9): pp. 1059-1068, Sep. 2002.

Wahle et al., 3D Heart Vessel Reconstruction from Biplane Angiograms, IEEE Computer Graphics and Applications, 16(1): pp. 65-73, Jan. 1996.

Helmut Mair et al., Epicardial Lead Implantation Techniques for Biventricular Pacing via Left Lateral Mini-Thoracotomy, Video Assisted Thoracoscopy and Robotic Approach, The Heart Surgery Forum, 6(5): pp. 412-417, Mar. 2003.

J. L. Cox, J. P. Boineau, R. B. Schuessler, T. B. Ferguson, Jr., M. E. Cain, B. D. Lindsay, P. B. Corr, K. M. Kater, D. G. Lappas; "Operations for Atrial Fibrillation;" Electrophysiology, Pacing and Arrhythmia, Clin. Cardiol. 14, 1991; pp. 827-834.

W. M. Feinberg, J. L. Blackshear, A. Laupacis, R. Kronmal, and R. G. Hart; "Prevalence, Age Distribution, and Gender of Patients with Atrial Fibrillation;" Arch Intern Med., vol. 155, Mar. 13, 1995; pp. 469-473.

M. Haissaguerre, P. Jais, S. C. Shah, A. Takahashi, M. Hocini, G. Quiniou, S. Garrigue, A. Le Mouroux, P. Le Metayer, and J. Clementy; "Spontaneous Initiation of Atrial Fibrilliation by Ectopic Beats Originating in the Pulmonary Viens;" The New England Journal of Medicine, vol. 339, No. 10, Sep. 3, 1998; pp. 659-668.

C. Pappone, S. Rosanio, G. Augello, G. Gallus, G. Vicedomini, P. Mazzone, S. Gulletta, F. Gugliotta, A. Pappone, V. Santinelli, V. Tortoriello, S. Sala, A. Zangrillo, G. Crescenzi, S. Benussi, and O. Alfieri; "Mortality, Morbidity, and Quality of Life After Circumferential Pulmonary Vein Ablation for Atrial Fibrillation;" Journal of the American College of Cardiology, vol. 42, No. 2; 2003; 185-197.

"Current Problems in Cardiology—Atrial Fibrilliation: Epidemiology, Mechanisms, and Management;" Current Problems in Cardiology, Jul. 2000; pp. 406-524.

ACC/AHA/ESC Practise Guidelines; Eur. Heart J., vol. 22, issue 20, Oct. 2001; pp. 1854-1923.

M. D. Leash, T. Trepelse, H. Omran, A. Bartorelli, P. Della Bella, T. Nakai, M. Reisman, D. fleschenberb, U. Krumsdorf, and D. Scherer; "Tiny Device Blocks 'Usless' Part of Heart, prevents blood clots;" Journal Report; American Heart Association; Apr. 9, 2002.

Ellen Barlow; "Operating in 3-D" found at www.med.harvard.edu/publications/HMAB/196fo3d.html.

H. Nikagawa et al., "Role of the Tricuspid Annulus and the Eustachian Valve/Ridge on Atrial Flutter: Relevance to Catheter Ablation of the Septal Isthmus and a New Technique for Rapid Identification of Ablation Success;" *Circulation* 1996; 94:407-24.

L. Gepstein et al., "A Novel Method for Nonfluoroscopic Catheter-Based Electroanatomical Mapping of the Heart: In Vitro and In Vivo Accuracy Results;" *Circulation* 1997; 95:1611-22.

S. Shpun et al., "Guidance of Radiofrequency Endocardial Ablation with Real-time Three-dimensional Magnetic Navigation System;" *Circulation* 1997; 96:2016-21.

J. Sra et al., "Electroanatomic Mapping to Identify Breakthrough Sites in Recurrent Typical Human Flutter;" *Paceing Clin. Electrophysiol* 2000; 23:1479-92.

R.J. Schilling et al.; "Simultaneous Endocardial Mapping in the Human Left Ventricle Using a Noncontact Catheter: Comparision of Contact and Reconstructed Electrograms During Sinus Rhythm;" *Circulation* 1998; 98:997-98.

C. C. Gornick et al., "Validation of a New Noncontact Catheter System for Electroanatomic Mapping of Left Ventricular Endocardium;" *Circulation* 1999; 99:829-835.

J. Sra et al., "Noncontact Mapping for Radiofrequency Ablation of Complex Cardiac Arrhythmias;" *J. Interven. Cardiac Electrophysiol* 2001; 5:323-331.

N. M.S. de Groot et al., "Three-Dimensional Catheter Positioning During Radiofrequency Ablation in Patients: First Application of a Real-Time Position Management System;" *J. Interven. Cardiac Electrophysiol* 2001; Nov. 11(11):1183-92.

J. Schreieck et al., "Radiofrequency Ablation of Cardiac Arrhythmias Using a Three-Dimensional Real-Time Position Management and Mapping System;" *Pacing Clin. Ekectrophysiol*, Dec. 2002, 25(12):1699-707.

F. Wittkampf et al., "Real-Time, Three-Dimensional, Nonfluoroscopic Localization of the Lasso Catheter;" *J. Interven. Cardiac Electrophysioll* 2002, 13:630.

J. Sra et al., "Cardiac Chamber Geometry Construction, Catheter Navication and Ablation Using Cutaneous Patches;" *Supplement to Circulation* Oct. 2003, 108 (17): IV-585, Abstract 2667.

J. Sra et al., "Three-Dimensional Right Atrial Geometry Construction and Catheter Tracking Using Cutaneous Patches;" *J. Interven. Cardiac Electrophysiol*, 2003 14:897.

Z. Zhang; "Iterative Point Matching for Registration of Free-Form Curves;" *Inria* 1992, pp. 1-40.

C.L. Grines et al.; "Functional Abnormalities in Isolated Left Bundle Branch Block: The Effect of Interventricular Asynchrony;" *Circulation*; 1989; 79:845-53.

H. B. Xia et al., "Differing effects of right ventricular pacing and left bundle branch block on left ventricular function," *Br. Heart J.*, 1993; 69:166-173.

S. Cazeau et al., "Effects of Multisite Biventricular Pacing in Patients with Heart Failure and Intraventricular Conduction Delay," *N. Engl. J. Med.* 2001; 344:873-880.

M. V. Pitzalis et al., "Cardiac Resynchronization Therapy Tailored by Echocardiographic Evaluation of Ventricular Acnchrony;" *J. Am. Coll. Cardiol.* 2002; 40:1615-22.

W. T. Abraham et al., "Cardiac Resynchronization in Chronic Heart Failure;" *N. Engl. J. Med.* 2002; 346:1845-1853.

C. A. Pelizzari et al., "Accurate Three-Dimensional Registration of CT, PET, and/or MR Images of the Brain;" *J. Comput. Assist. Tomogr.* 1989; 13:20-26.

A.C. Evans et al.; "MRI-PET Correlation in Three-Dimensions Using a Volume-of-Interest (VOI) Atlas;" *J. Cerb Flow Metab.* 1991; 11:A69-A78.

R.P. Woods et al.; "Rapid Automated Algorithm for Aligning and Reslicing PET Images;" *Journal of Computer Assisted Tomography*, 1992; 16:620-633.

B.A. Ardekani et al.; "A Fully Automatic Multimodality Image Registration Algorithm;" *Journal of Computer Assisted Tomography*; 1995; 19:615-623.

L. Thurfell et al.; "Registration of Neuroimaging Data: Implementation and Clinical Applications;" *American Society of Neuroimaging*; 2000; 10:39-46.

S. A. Ben-Haim et al.; "Nonfluoroscopic, in vivo navigation and mapping technology;" *Nature Medicine*; 1996, 2:1393-5.

B. Taccardi et al.; "A new intracaitary probe for detecting the site of origin of ectopic ventricular beats during one cardiac cycle;" *Circulation*; 1987; 75:272-81.

F. H.M. Wittkampf et al.; "New Technique for Real-Time 3-Dimensional Localization of Regular Intracardiac Electrodes;" *Circulation*; 1999; 99:1312-17.

V. Fuster et al. "ACC/AHA/NASPE 2002 Guidelines Update for Implantation of Pacemakers and Antiarrhythmia Devices;"*J. Am. Coll. Cardiol* 2001; 38:1-47.

D. R. Ney "Volumetric Rendering of Computed Tomography Data: Principles and Techniques;" *IEEE Computer Graphics and Applications*, 1990; 24-32.

N. M. Alpert et al., "The Principal Axes Transformation—A Method for Image Registration;" *The Journal of Nuclear Medicine*; 1990; 31:1717-1722.

P.A. van den Elsen et al.; "Medical Image Matching—A Review with Classification;" *IEEE Engineering in Medicine and Biology*, 1993; 26-38.

G. T. Barnes et al.; "Conventional and Spiral Computed Tomography: Physical Principles and Image Quaility Considerations;" *Computed Body Tomography*, 1998, Lippincot-Raven, Philadelphia, PA pp. 1-20.

Milan Sonka and J. Michael Fitzpatrick (eds); *Handbook of Medical Imaging Vol. 2. Medical Image Processing and Analysis*; pp. 129-174 & 447-506.

W. M. Feinberg et al.; "Prevalence, Age Distribution, and Gender of Patients with Atrial Fibrillation;" *Arch. Intern. Med. Vol. 155*; Mar. 1995; pp. 469-473.

*J. L. Cox, J. P. Boineau, R. B. Schuessler, T. B. Ferguson, Jr., M. E. Cain, B. D. Lindsay, P. B. Corr, K. M. Kater, D. G. Lappas; "Operations for Atrial Fibrilliation;" Electrophysiology, Pacing and Arrhythmia, Clin. Cardiol. 14, 1991; pp. 827-834.

*M. Haissagume, P. Jais, S. C. Shah, A. Takahashi, M. Hocini, G. Quiniou, S. Garrigue, A. Le Mouroux, P. Le Metayer, and J. Clementy; "Spontaneous Initiation of Atrial Fibrilliation by Ectopic Beats Originating in the Pulmonary Viens;" The New England Journal of Medicine, vol. 339, No. 10, Sep. 3, 1998; pp. 659-668.

*C. Pappone, S. Rosanio, G. Augello, G. Gallus, G. Vicedomini, P. Mazzone, S. Gulletta, F. Gugliotta, A. Pappone, V. Santinelli, V. Tortoriello, S. Sala, A. Zangrillo, G. Crescenzi, S. Benussi, and O. Alfieri; "Mortality, Morbidity, and Quality of Life After Circumferential Pulmonary Vein Ablation for Atrial Fibrillation;" Journal of the American College of Cardiology, vol. 42, No. 2; 2003; 185-197.

*J. Sra et al., "Current Problems in Cardiology—Atrial Fibrilliation: Epidemiology, Mechanisms, and Management;" Current Problems in Cardiology, Jul. 2000; pp. 406-524.

*ACC/AHA/ESC Practise Guidelines; Eur. Heart J., vol. 22, issue 20, Oct. 2001; pp. 1854-1923.

*M. D. Leash, T. Trepelse, H. Omran, A. Bartorelli, P. Della Bella, T. Nakai, M. Reisman, D. fleschenberb, U. Krumsdorf, and D. Scherer; "Tiny Device Blocks 'Usless' Part of Heart, prevents blood clots;" Journal Report; American Heart Association; Apr. 9, 2002.

*Ellen Barlow; "Operating in 3-D" found at www.med.harvard.edu/publications/HMAB/196fo3d.html.

"Surgical Planning System with Real-Time Volume Rendering"; Inventors: Young Chong Loh, et al.; Proceedings of the International Workshop on Medical Imaging and Augmented Reality; pp. 259-261; Jun. 30, 2001.

Chinese Office Action for Patent Application No. 200480024608.2; Application Date: Jun. 30, 2004; Title: "Cardiac Imaging System and Method for Planning Surgery"; Date of Issue: Jul. 10, 2009.

English Abstract for JP2002-143179; Publication Date: May 21, 2002; 1pg.

Helumut Gulbins et al., Preoperative 3D-Reconstructions of Ultra-CT Images for the Planning of Minimally Invasive Direct Coronary Artery Bypass Operation (MIDCAB), Heat Surgery Forum vol. 1, Issue 2, pp. 111-115, http://static. cjp.com/gems/pdfs/1988-4092.pdf.

English Translation of Reasons for Rejection issued by the Japanese Patent Office, citing JP2002143179 in connection with Japanese Patent Application No. 2006-517777; 4 pgs.

* cited by examiner

CARDIAC IMAGING SYSTEM AND METHOD FOR PLANNING MINIMALLY INVASIVE DIRECT CORONARY ARTERY BYPASS SURGERY

CROSS REFERENCE TO RELATED APPLICATIONS

This application claims the benefit of U.S. provisional application No. 60/484,012, filed Jul. 1, 2003, the contents of which are incorporated by reference herein in their entirety.

BACKGROUND OF THE INVENTION

The present disclosure relates generally to cardiac surgical bypass systems and, more particularly, to a cardiac imaging system and method for planning minimally invasive direct coronary artery bypass surgery (MIDCAB).

According to American Heart Association statistics, over 500,000 coronary artery bypass grafts (CABGs) are performed every year in the United States alone. In coronary artery disease, the arteries that bring blood to the heart muscle (i.e., the coronary arteries) become clogged by plaque, which is a buildup of fat. During CABG surgery, the blood is rerouted around the clogged arteries in order to improve blood flow and oxygen to the heart. A healthy blood vessel, such as the left internal mammary, is detached from the chest wall and is thereafter used to circumvent the blocked area. Alternatively, a segment of vein from the leg can also be used for the CABG. One end of the vessel/vein is sewn onto the aorta (the large artery leaving the heart), while the other end is attached or "grafted" to the coronary artery beyond (or past or distal to) the blocked area. Patients may undergo multiple by-passes at the same time.

Cardiopulmonary bypass using a heart-lung machine is typically used to stop the movement of the heart at the time of the CABG procedure. Although CABG is the treatment of choice in many cases (and is one of the most common surgical procedures performed today), there are several potential complications from this surgery, as well as from the cardiopulmonary bypass technique required during the CABG procedure. In a recent study published in the New England Journal of Medicine, 53 percent of patients had diminished mental acuity at the time of discharge from the hospital after a CABG procedure. In addition to the prolonged hospital stay and the possible need for transfusions, sternal wound infection at the site of the incision can occur in 1 to 4 percent of patients and carries a mortality (death) rate of about 25 percent. Furthermore, as many as 8 percent of patients may develop kidney dysfunction as a result of the CABG procedure.

As a result of the above described problems associated with CABG, minimally invasive direct coronary artery bypass (MIDCAB) surgery has been used as an alternative in some patients, wherein the MIDCAB procedure does not require reliance on the heart-lung machine. In MIDCAB surgery, a 10-12 cm access incision is made in the patient's chest, after which several different instruments are used to stabilize the heart at the time of surgery. The surgeon then connects a graft to the diseased coronary arteries while the heart is beating without artificial support. Due to the nature of the operation, grafting (the attaching of the vessels) must be done under the surgeon's direct vision and the coronary artery that is to be bypassed must lie directly beneath the incision (surgical opening). Consequently, this procedure is currently used in only a limited number of patients, and only if it is known that just one or two of the arteries require a bypass.

Although it is estimated that over 30 percent of patients who need CABG may be suitable candidates for MIDCAB surgery, presently the procedure is performed in only 10 percent of patients because of this unknown factor. There is, therefore, a distinct need for an improved system and method to make this procedure more effective and easier to perform.

BRIEF DESCRIPTION OF THE INVENTION

The above discussed and other drawbacks and deficiencies of the prior art are overcome or alleviated by a method for planning minimally invasive direct coronary artery bypass surgery (MIDCAB) for a patient. In an exemplary embodiment, the method includes obtaining acquisition data from a medical imaging system, and generating a 3D model of the coronary arteries and one or more cardiac chambers of interest. One or more anatomical landmarks are identified on the 3D model, and saved views of the 3D model are registered on an interventional system. One or more of the registered saved views are visualized with the interventional system.

In another embodiment, a method for planning minimally invasive direct coronary artery bypass surgery (MIDCAB) for a patient includes obtaining acquisition data from a medical imaging system using a protocol directed toward the coronary arteries and left ventricle. The acquisition data is segmented using a 3D protocol so as to visualize the coronary arteries and the left ventricle. A 3D model of the coronary arteries and the left ventricle of the patient is generated, and one or more anatomical landmarks on the 3D model are identified. Saved views of the 3D model are registered on an interventional system, and one or more of the registered saved views are visualized the interventional system. The orientation and any anomalies associated with the coronary arteries and the left ventricle are identified from the 3D model.

In still another embodiment, a method for planning minimally invasive direct coronary artery bypass surgery (MIDCAB) for a patient includes obtaining acquisition data from a cardiac computed tomography (CT) imaging system using a protocol directed toward the coronary arteries and left ventricle. The acquisition data is segmented using a 3D protocol so as to visualize the coronary arteries and left ventricle, including interior views of the coronary arteries. A 3D model of the coronary arteries and left ventricle of the patient is generated, and one or anatomical landmarks on the 3D model are identified. Saved views of the 3D model are registered on a fluoroscopy system, and one or more of the registered saved views are visualized with the fluoroscopy system. The orientation and any anomalies associated with the coronary arteries and the left ventricle are identified from the 3D model.

In still another embodiment, a system for planning minimally invasive direct coronary artery bypass surgery (MIDCAB) for a patient includes a medical imaging system for generating acquisition data, and an image generation subsystem for receiving the acquisition data and generating one or more images of the coronary arteries and the left ventricle of the patient. An operator console is configured for identifying one or more anatomical landmarks on one or more of the generated images, and a workstation includes post processing software for registering saved views of the 3D model on an interventional system. The interventional system is configured for visualizing one or more of the registered saved views therewith, quantifying distance and location information for a cardiac point of interest, and identifying an incision location and path for MIDCAB based on the quantified distance and location information for the cardiac point of interest.

BRIEF DESCRIPTION OF THE DRAWINGS

Referring to the exemplary drawings wherein like elements are numbered alike in the several Figures.

DETAILED DESCRIPTION OF THE INVENTION

Disclosed herein is a cardiac imaging system and method for planning minimally invasive direct coronary artery bypass surgery (MIDCAB), so as to enable a practitioner (e.g., electrophysiologist, cardiologist, surgeon) to plan in advance the approach to take for the procedure. With more detailed 3D and navigator (interior) views, a geometric representation of the coronary arteries and the left ventricle (LV) is obtained with an imaging modality such as CT, magnetic resonance imaging or ultrasound. The practitioner can then identify the orientation, size, anomalies, and extent of blockage in the coronary arteries to be targeted for MIDCAB. Using this information, a more exact approach can be taken for the MIDCAB, with incisions made at the most appropriate sites, allowing for more areas to be targeted and, at the same time, allowing for smaller incisions.

Although the exemplary embodiments illustrated hereinafter are described in the context of a computed tomography (CT) imaging system, it will be appreciated that other imaging systems known in the art (e.g., magnetic resonance, ultrasound, 3D fluoroscopy) are also contemplated with regard to planning MIDCAB.

Figure 1:
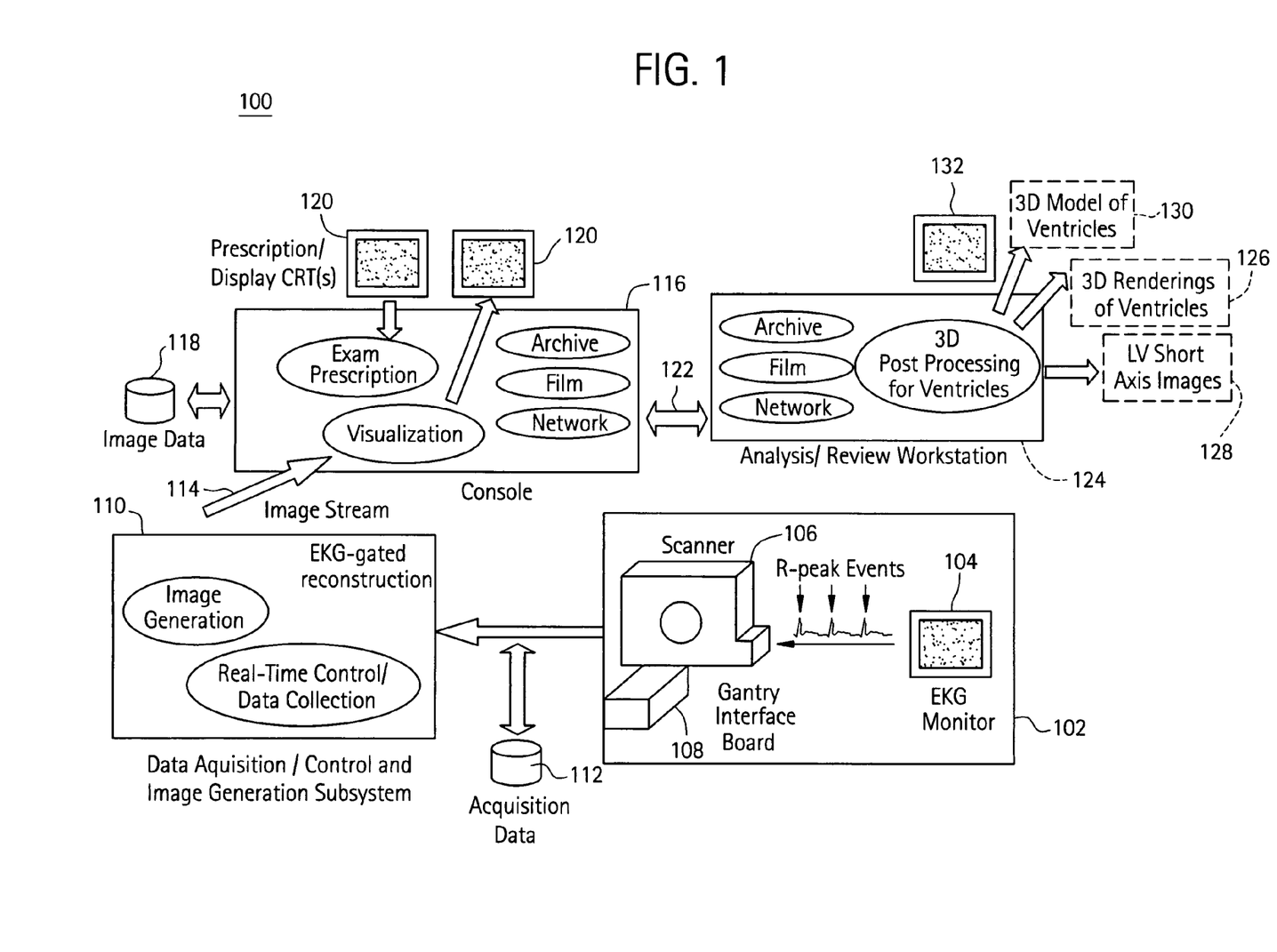
FIG. 1 is a schematic diagram of a medical imaging system, such as a computed tomography (CT) system, suitable for planning minimally invasive direct coronary artery bypass (MIDCAB), in accordance with an embodiment of the invention.

Referring now to FIG. 1, there is shown an overview of an exemplary cardiac computed tomography (CT) system 100 with support for cardiac imaging. Again, it should be understood that the cardiac CT system 100 is presented by way of example only, since other imaging systems known in the art (e.g., magnetic resonance, ultrasound, 3D fluoroscopy) may also be used in an embodiment of the present invention. A scanner portion 102 of the system 100 includes an EKG monitor 104 that outputs Revents into a scanner 106 through a scanner interface board 108. A suitable example of scanner interface board 108 is a Gantry interface board, and can be used to couple an EKG system to the scanner. The cardiac CT subsystem defined by scanner portion 102 utilizes EKG-gated acquisition or image reconstruction capabilities to image the heart (and more specifically the coronary arteries and left ventricle) free of motion in its diastolic phase, as well as in multiple phases of systole and early diastole.

Data are outputted from the scanner portion 102 into a subsystem 110 that includes software for performing data acquisition, data control and image generation. In addition, data that is outputted from the scanner 106, including Rtime stamps, is stored in an acquisition database 112. Acquisition is performed according to one or more acquisition protocols that are optimized for imaging the heart and specifically the coronaries and LV in diastole and multiple phases in systole and early diastole. Image generation is performed using one or more optimized 3D protocols for automated image segmentation of the CT image dataset for identifying the orientation, size and any anomalies of the coronary arteries. The 3D protocols are further optimized to generate navigator (interior) views of the coronaries to assess the size and extent of the lesions therein.

The image data stream 114 is sent to an operator console 116. The data used by software at the operator console 116 for exam prescription and visualization is stored in an image database 118, along with the data from the image data stream 114. Display screens 120 are provided to the operator of the exam prescription and visualization processes. The image data may be archived, put on film or sent over a network 122 to a workstation 124 for analysis and review, including 3D post processing. The post processing software depicted in the workstation 124 includes one or more optimized 3D protocols and short axis protocols from an automated image segmentation of the CT image dataset for the LV anatomy, movement of LV walls during systole (i.e., LV contractility), epicardial fat location, location of viable tissue, blood vessels and their branches and orientation.

The 3D protocols and short axis protocols of the post processing software enable the software to provide views of the LV, including blood vessels, branches and slow motion cine of the LV, particularly the posterolateral wall or other areas of the LV. These special views and video (cine) clips may be saved into a 3D rendering of ventricle files 126 and LV short axis images 128 for use by the practitioner for interventional planning and procedure. The post processing software also provides for the export of detailed 3D models 130 of the thoracic wall and ventricle surfaces. The 3D models 130 (which may be implemented through color coding, contouring, movie views, etc.) may be viewed on display screen 132 associated with workstation 124 and are configured to include geometric markers inserted into the volume at landmarks of interest such that the thoracic wall and the LV are visualized in a translucent fashion with the opaque geometric landmarks.

In addition, the 3D models 130 may be in exported in any of several formats, including but not limited to: a wire mesh geometric model, a set of contours, a segmented volume of binary images, and a DICOM (Digital Imaging and Communications in Medicine) object using the radiation therapy (RT) DICOM object standard or similar object. Other formats known in the art can also be used to store and export the 3D models 130.

Figure 2:
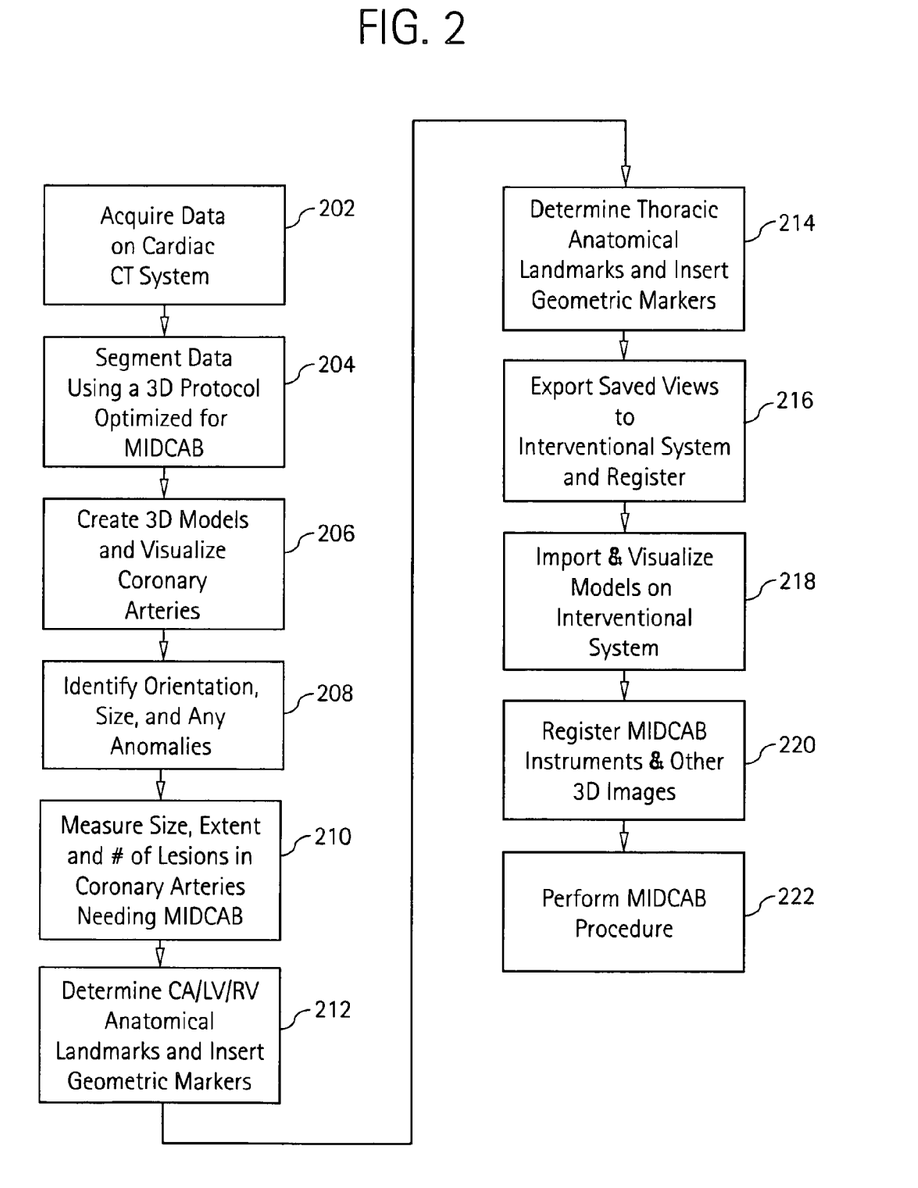
FIG. 2 is a flow diagram of a method for planning minimally invasive direct coronary artery bypass (MIDCAB), in accordance with a further embodiment of the invention.

Referring now to FIG. 2, there is shown a flow diagram 200 illustrating a method for MIDCAB planning, in accordance with a further embodiment of the invention. Beginning at block 202, a volume of data is initially acquired on the cardiac CT system, using a protocol that is preferably optimized for the coronaries and LV regions of the heart. A continuous sequence of consecutive images is collected from a volume of a patient's data, in which a shorter scanning time using faster scanners and synchronization of the CT scanning with the QRS (peak) on the ECG (Electrocardiogram) signal will reduce motion artifacts (e.g. blurring, shadowing, streaking) in a beating organ like the heart. The ability to collect a volume of data with a short acquisition time allows reconstruction of images that have more precise depictions of anatomical landmarks, making them easier to understand.

At block 204, the image dataset is segmented with post-processing software using a 3D protocol and short axis protocols optimized for MIDCAB. Automated or semi-automated procedures may be employed, where appropriate, with or without queues from the operator. This operation can be performed on short axis reformatted cardiac images for each phase and slice location to obtain the displacement profile, or on multiphase, long axis reformatted cardiac images.

Then, as shown in block 206, the coronary arteries and LV are visualized using 3D surface and/or volume rendering to create 3D models thereof that provide certain quantitative features of the coronaries and the ventricles such as contour, position, orientation, dimensions of the coronaries and the ventricles and, additionally, the function and the areas of scarred tissue of the ventricles. As shown in block 208, the orientation, size and extent of the lesions in the coronary arteries targeted for MIDCAB are identified. In this manner, the size and contour of the vessels as well as the size and extent of the lesions are measured and determined, as shown in block 210.

Figure 3:
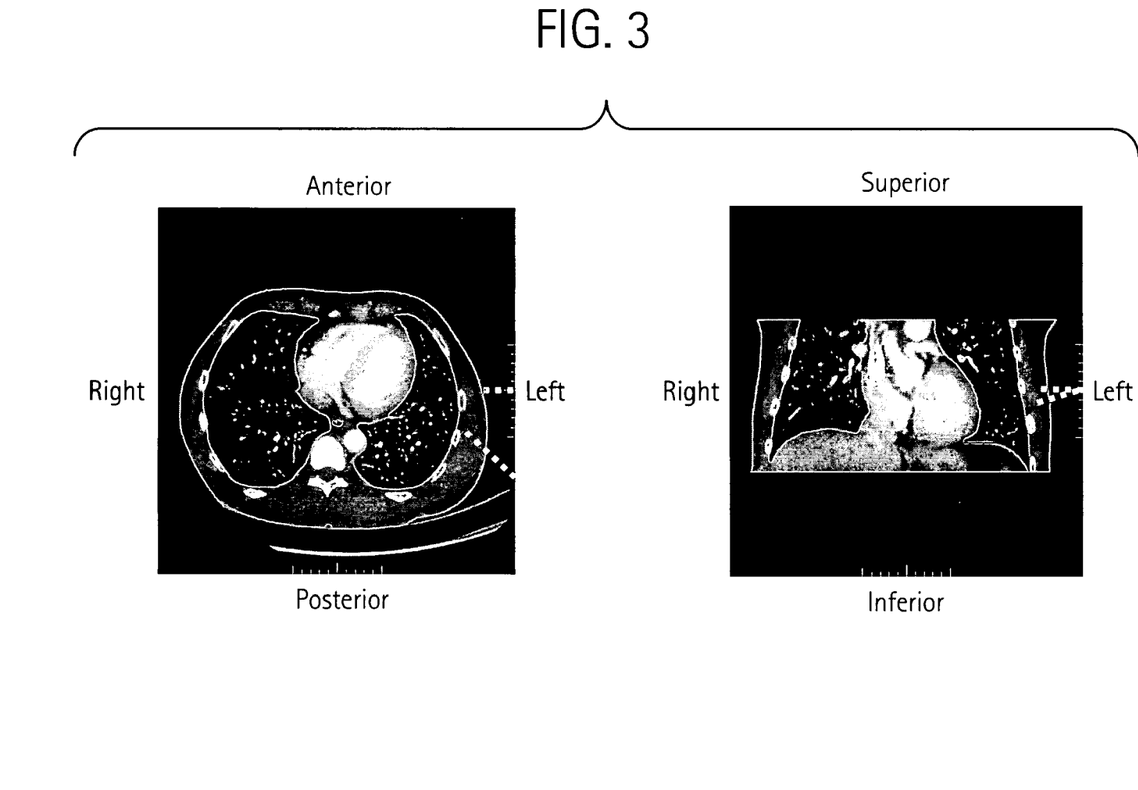
FIG. 3 is an exemplary CT image of the chest and heart, on which distance and angles may be measured for MIDCAB planning.

For example, FIG. 3 illustrates an exemplary CT image of the chest and heart and their spatial relationship there between. Exact distances and angles may be measured in 3D for planning MIDCAB and, in addition, such information may also be used to generate thickness graphs or plots, as well as 3D geometric visualization for quick analysis. This information can contribute significantly to identification and isolation of the optimal path through the chest wall.

Figure 4:
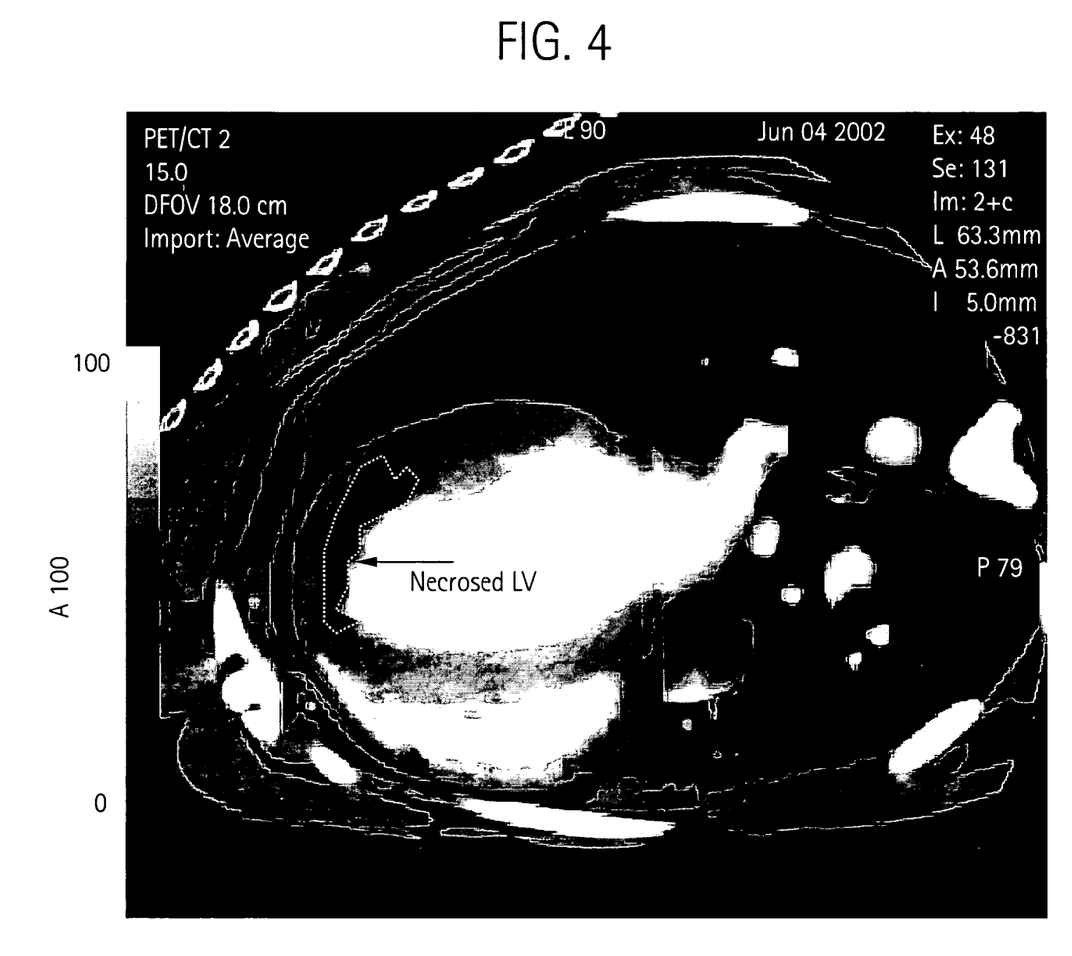
FIG. 4 is a cardiac CT image showing necrosed LV due to myocardial infarction.

Referring again to FIG. 2, method 200 proceeds to block 212 for identification of anatomical landmarks over the thoracic wall, coronary arteries and ventricles. At block 214, explicit geometric markers are then inserted into the volume at landmarks of interest, wherein the markers may be visualized in a translucent fashion using 3D surface and/or volume rendering so as not to obscure the image. An example of such a visualization is presented in FIG. 4, which illustrates a cardiac CT image showing a necrosed LV due to myocardial infarction. The specific images (e.g., Dicom images, video clips, films, etc.) are saved as desired for subsequent reference during the MIDCAB. As shown in block 216 of FIG. 2, the saved views are then exported and registered with the computer workstation of the interventional system. After the registered images are imported, they may be visualized over the interventional system by the practitioner, as seen in block 218.

In addition to the registering markers, the workstation of the interventional system may also configured to register the instruments used for the specific MIDCAB procedure, as shown in block 220. Finally, the actual MIDCAB surgery is performed at block 222.

It will be appreciated that automatic techniques may be employed to perform any of the above steps by using one or more of the several computer-assisted detection, localization and visualization methods available. Such steps may include, for example, quantitative analysis of defects, localized contractility profile (LV wall movement), and identification of blood vessels using the continuity of same intensity levels. Moreover, these methods could be either completely automatic when the procedure and the organ of interest is specified or partly interactive with input from the user.

It will further be appreciated that through the use of the above described method and system embodiments, the planning of MIDCAB is improved in that the imaging information generated and registered allows for an appropriately tailored approach to the interventional procedure. In choosing the appropriate approach, the duration of the procedure itself is reduced and any unnecessary procedures are also eliminated. More particularly, a detailed 3D geometric and axial representation of the coronary arteries and LV increases the precision of the MIDCAB procedure. The identification of necrosed myocardium, if any, enables the practitioner to avoid such areas and determine an exact location of the incision is determined in advance before the surgery is performed.

The above described planning process thus reduces the amount of time required to perform the MIDCAB. Moreover, the identification of appropriate locations increases the efficacy of treatment and can reduce the risk of complications. After the procedure is completed, the data can be archived, read and processed in the form of CD-ROMs, floppy diskettes, hard drives or any other mediums used for this purpose as in the acquisition and transportation stages. Thus, the computer and the medium also become an apparatus for the purposes of the present invention.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for planning a minimally invasive direct coronary artery bypass (MIDCAB) for a patient, the method comprising:
    obtaining acquisition data from a medical imaging system;
    generating a 3D model of coronary arteries and one or more cardiac chambers of interest of the patient from said acquisition data, prior to performing said MIDCAB;
    identifying one or more anatomical landmarks on said 3D model and inserting corresponding translucent geometric markers thereat, utilizing user input at an operator console;
    saving views of said 3D model in a database;
    measuring sizes of lesions and a number of the lesions in the coronary arteries utilizing said 3D model;
    registering said saved views of said 3D model on a workstation of an interventional system, said saved views of said 3D model having said translucent geometric markers, said registering including importing said saved views of said 3D model having said translucent geometric markers to the coordinate system of said interventional system using said one or more anatomical landmarks;
    visualizing one or more of said registered saved views on a display screen of said interventional system; and
    utilizing the interventional system to quantify distance and location information for a cardiac point of interest prior performing said MIDCAB; and
    identifying an incision location and path for said MIDCAB based on said quantified distance and location information for said cardiac point of interest.

2. The method of claim 1, further comprising identifying, from said 3D model, orientation, size and dimensions of the coronary arteries.

3. The method of claim 1, wherein said obtaining acquisition data is implemented with protocols directed for imaging the coronary arteries.

4. The method of claim 3, further comprising utilizing post processing software to process said acquisition data so as to generate interior views of the coronary arteries.

5. The method of claim 1, further comprising registering MIDCAB instruments on said interventional system.

6. The method of claim 1, wherein said obtaining acquisition data is EKG gated.

7. A method for planning a minimally invasive direct coronary artery bypass (MIDCAB) for a patient, the method comprising:
obtaining acquisition data from a medical imaging system using a protocol directed toward the coronary arteries and left ventricle;
segmenting said acquisition data using a 3D protocol so as to visualize the coronary arteries and the left ventricle;
generating a 3D model of the coronary arteries and the left ventricle of the patient from said acquisition data, prior to performing said MIDCAB;
identifying one or more anatomical landmarks on said 3D model and inserting corresponding translucent geometric markers thereat, utilizing user input at an operator console;
saving views of said 3D model in a database;
measuring sizes of lesions and a number of lesions in the coronary arteries utilizing said 3D model and identifying, from said 3D model, an orientation and any anomalies associated with the coronary arteries;
registering said saved views of said 3D model on a workstation of an interventional system, said saved views of said 3D model having said translucent geometric markers, said registering including, transforming said saved views of said 3D model having said translucent geometric markers to the coordinate system of said interventional system using said one or more anatomical landmarks;
visualizing one or more of said registered saved views on a display screen of said interventional system; and
using said identified orientation and anomalies associated with the coronary arteries and said registered saved views to determine appropriate sites for incisions for targeted MIDCAB.

8. The method of claim 7, further comprising utilizing post processing software to process said acquisition data so as to generate interior views of the coronary arteries and the left ventricle.

9. The method of claim 8, wherein said 3D model and said interior views are visualized through the display screen associated with said interventional system.

10. The method of claim 7, wherein said obtaining acquisition data is EKG gated.

11. The method of claim 7, further comprising registering MIDCAB instruments on said interventional system.

12. A method for planning a minimally invasive direct coronary artery bypass (MIDCAB) for a patient, the method comprising:
obtaining acquisition data from a cardiac computed tomography (CT) imaging system using a protocol directed toward coronary arteries and one or more cardiac chambers of interest;
segmenting said acquisition data using a 3D protocol so as to visualize the coronary arteries, including interior views of the coronary arteries;
generating a 3D model of the coronary arteries of the patient from said acquisition data, prior to performing said MIDCAB;
identifying one or more anatomical landmarks on said 3D model and inserting corresponding translucent geometric markers thereat, utilizing user input at an operator console;
saving views of said 3D model in a database;
measuring sizes of lesions and a number of the lesions in the coronary arteries utilizing said 3D model and identifying, from said 3D model, an orientation and anomalies associated with the coronary arteries;
registering said saved views of said 3D model on a fluoroscopy system, said saved views of said 3D model having said geometric markers, said registering including transforming said saved views of said 3D model having said translucent geometric markers to the coordinate system of the fluoroscopy system using said one or more anatomical landmarks;
visualizing one or more of said registered saved views with said fluoroscopy system; and
quantifying distance and location information for a cardiac point of interest; and
identifying an incision location and path for said MIDCAB based on said quantified distance and location information for the cardiac point of interest.

13. The method of claim 12, further comprising utilizing post processing software to process said acquisition data so as to generate interior views of the coronary arteries.

14. The method of claim 12, wherein said 3D model and said registered saved views are visualized through a display screen associated with said fluoroscopy system.

15. The method of claim 12, wherein said obtaining acquisition data is EKG gated.

16. The method of claim 12, further comprising registering MIDCAB instruments on said interventional system.

17. A system for planning a minimally invasive direct coronary artery bypass (MIDCAB) for a patient, comprising:
a medical imaging system for generating acquisition data;
an image generation subsystem for receiving said acquisition data and generating a 3D model of coronary arteries and one or more cardiac chambers of interest of the patient, the image generation subsystem further configured to automatically measure sizes of lesions and a number of the lesions in the coronary arteries utilizing said 3D model;
an operator console configured to receive user input to identify one or more anatomical landmarks on said 3D model and to insert corresponding geometric markers thereat, said console further configured to save views of said 3D model having said geometric markers to a database;
a workstation of an interventional system configured to receive said saved views of said 3D model having said geometric markers from said database, where said workstation includes post processing software stored on a computer readable medium for registering said saved views of said 3D model on said interventional system by transforming said saved views of said 3D model having said geometric markers to the coordinate system of said interventional system using said one or more anatomical landmarks;
wherein said workstation of said interventional system is configured to:
import said registered saved views of said 3D model having said geometric markers;
visualize said registered saved views of said 3D model having said geometric markers; and
utilize said registered saved views of said 3D model having said geometric markers to quantify distance and location information for a cardiac point of interest to identify an incision location and path for MIDCAB.

18. The system of claim 17, wherein said image generation subsystem is configured with protocols directed for imaging the coronary arteries.

19. The system of claim 18, wherein said post processing software is further configured to process said acquisition data so as to generate interior views of the coronary arteries.

20. The system of claim 19, further comprising a display screen associated with said interventional system, said display screen for visualizing said 3D model and said interior views.

21. The system of claim 17, wherein said interventional system is configured for registering MIDCAB instruments therewith.

22. The method of claim 1, further comprising:
based on said registered saved views, identifying a location and path of an incision to reduce a size of the incision through a chest wall of the patient for MIDCAB.

23. The method of claim 7, further comprising:
based on said orientation and anomalies, identifying a location and path of an incision to reduce a size of the incision through a chest wall of the patient for MIDCAB.

24. The method of claim 12, further comprising:
based on said orientation and anomalies, identifying a location and path of an incision to reduce a size of the incision through a chest wall of the patient for MIDCAB.

* * * * *